United States Patent [19]
Peeters

[11] Patent Number: 5,741,787
[45] Date of Patent: Apr. 21, 1998

[54] ANTIGLUCOCORTICOID STEROIDS FOR THE TREATMENT OF ANXIETY DISORDERS

[75] Inventor: Bernardus Wynand Mathijs Marie Peeters, Herpen, Netherlands

[73] Assignee: Akzo Nobel N.V., Arnhem, Netherlands

[21] Appl. No.: 581,631

[22] PCT Filed: Jul. 28, 1994

[86] PCT No.: PCT/EP94/02513

§ 371 Date: Jan. 18, 1996

§ 102(e) Date: Jan. 18, 1996

[87] PCT Pub. No.: WO95/04536

PCT Pub. Date: Feb. 16, 1995

[30] Foreign Application Priority Data

Aug. 4, 1993 [EP] European Pat. Off. .............. 93202304

[51] Int. Cl.⁶ ............................................. A61K 31/56
[52] U.S. Cl. ........................... 514/177; 514/178; 514/181
[58] Field of Search ............................. 514/178, 181, 514/177

[56] References Cited

U.S. PATENT DOCUMENTS 5,232,917  8/1993  Bolger et al. ............................ 514/178

OTHER PUBLICATIONS

D.F. Papolos, *Brain Research*, 615 (1993) 304–309.

S.M. Korte et al., *Hormones and Behavior*, 27:167–183 (1993).

H.D. Veldhuis et al., *European Journal of Pharmacology*, 115(1985) 211–217.

E.R. De Kloet et al., *Neuroendocrinology*, 47:109–115 (1988).

*Primary Examiner*—James H. Reamer
*Attorney, Agent, or Firm*—William M. Blackstone; Mary E. Gormley

[57] ABSTRACT

The invention relates to the use of antiglucocorticoid steroids for the manufacture of a pharmaceutical composition for the treatment of anxiety disorders.

3 Claims, 2 Drawing Sheets

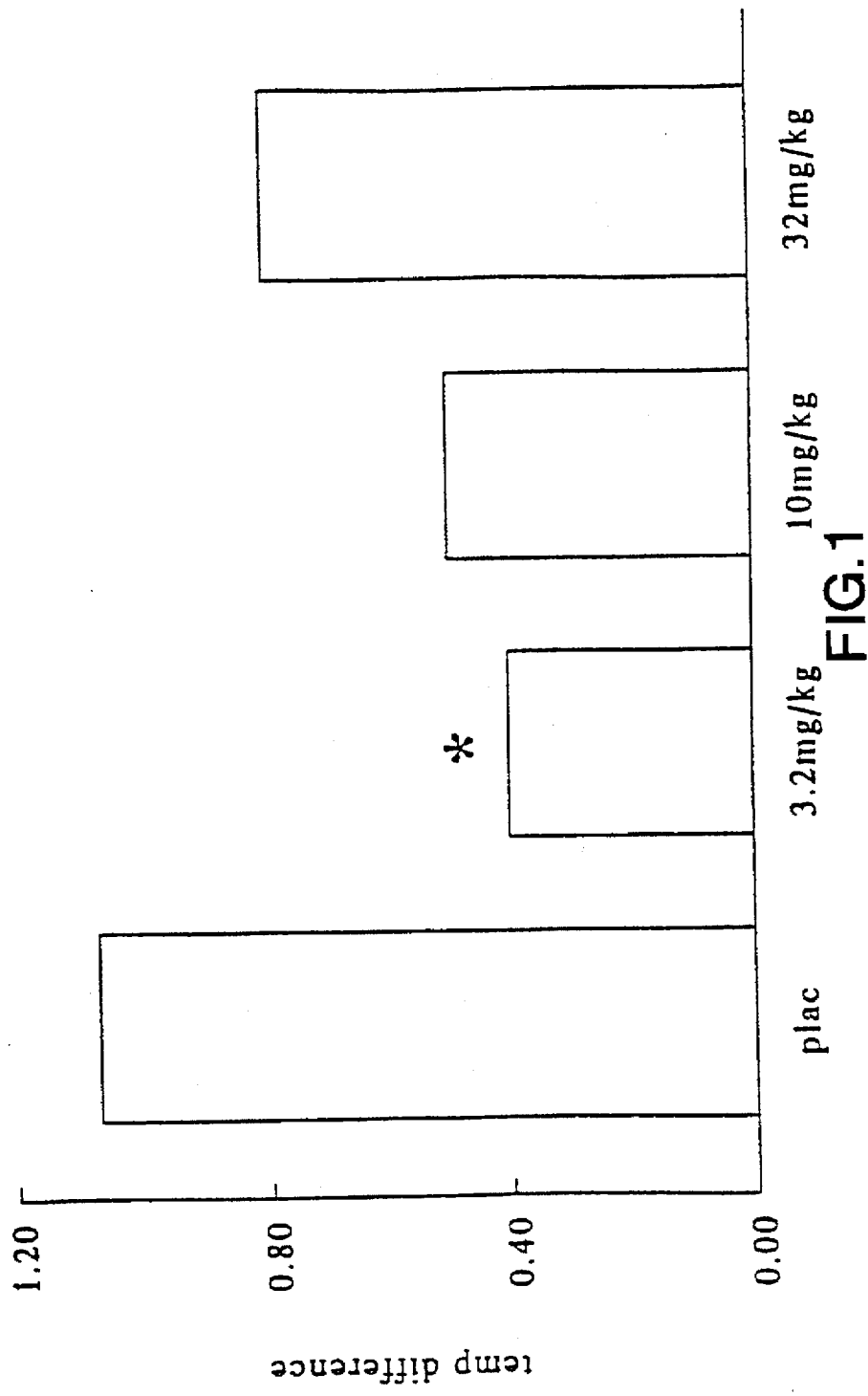

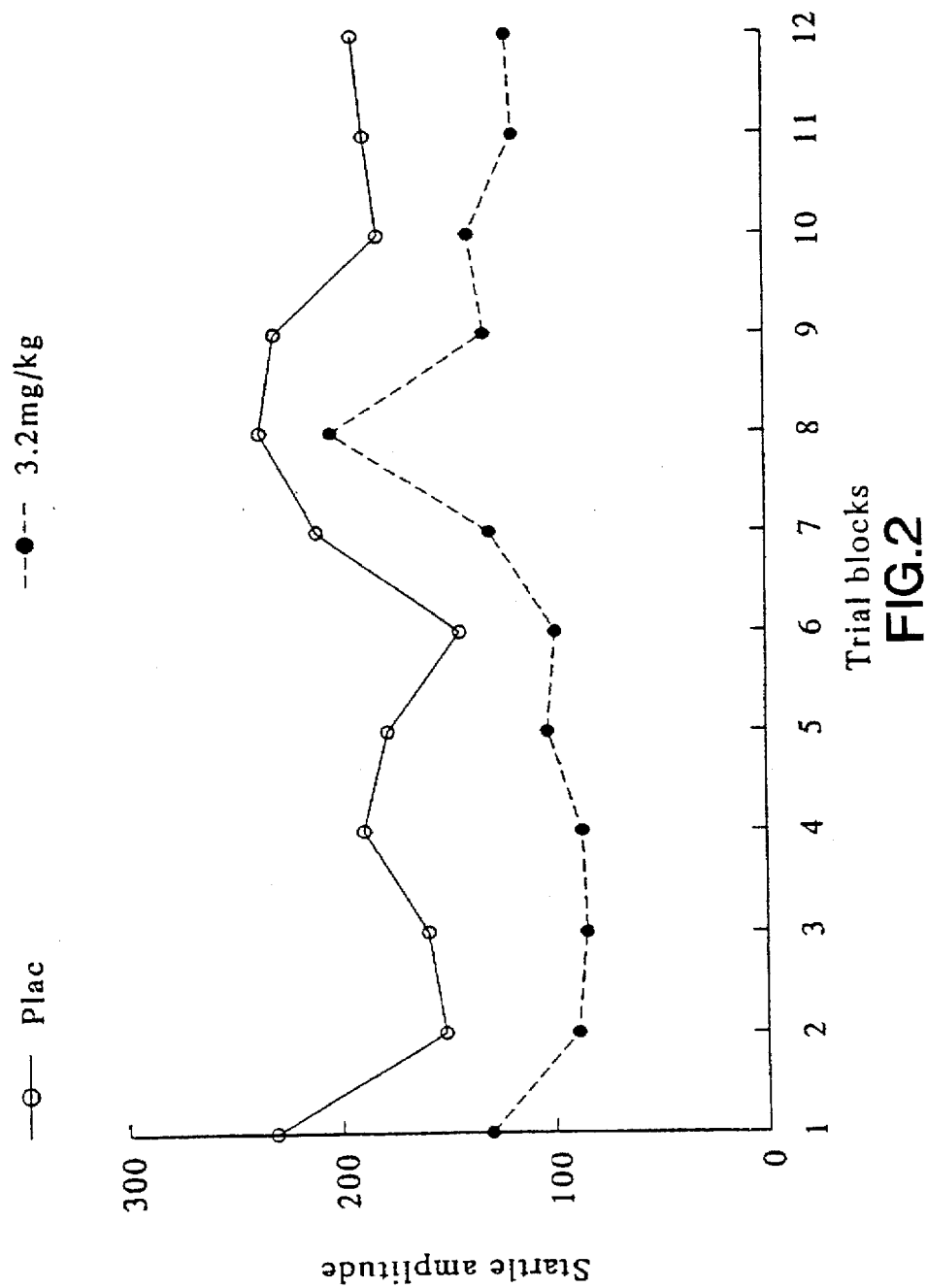

ANTIGLUCOCORTICOID STEROIDS FOR THE TREATMENT OF ANXIETY DISORDERS

FIELD OF THE INVENTION

The invention relates to the use of antiglucocorticoid steroids for the manufacture of a pharmaceutical composition for the treatment of anxiety disorders.

BACKGROUND OF THE INVENTION

Antiglucocorticoid steroids are a well known group of steroids which exhibits affinity for the glucocorticoid receptor (GR) and reduce completely or to a considerable extent the action of cortisol. For example, 11β-substituted steroids having antiglucocorticoid activity are disclosed in EP-A-190759 and EP-A-57115. Other steroids having antiglucocorticoid activity are 10β-substituted steroids as disclosed in EP-A-188396.

SUMMARY OF THE INVENTION

It has now been found that antiglucocorticoid steroids also exert anxiolytic effects, which make these steroids useful for the treatment of anxiety disorders. Anxiety disorder is a rather broad concept including for instance general anxiety, panic disorder, and various kinds of withdrawal symptoms (see: Diagnostic and Statistical Manual of Mental Disorders, 3 RD ED DSM-III, Washington, American Psychiatric Ass., p. 225–239, 1980).

The aim of this invention is to provide a pharmaceutical composition which can be used for the treatment or prevention of anxiety disorders.

Steroids that can be used for the treatment of anxiety disorders are known from WO 9303732. These steroids, however, have no hormonal effects and have no affinity to the glucocorticoid receptor: they activate the GABA receptor/chloride ionophore complex instead. No hint or suggestion towards the use of antiglucocorticoid steroids for the treatment or prevention of anxiety disorders is made in said publication. Antidepressant activity was suggested by De Kloet et al. (Neuroendocrinology, 47 (1988), 109–115) and by Veldhuis et al. (Eur. J. Pharmacol., 115 (1985) 211–217). However, since there is no relation between antidepressant and anxiolytic effects, no activity of antiglucocorticoid steroids for treating of preventing anxiety was suggested.

Benzodiazepines, such as librium and valium, are the most commonly used drugs for the treatment of anxiety disorders. However, these compounds are no steroids.

DETAILED DESCRIPTION OF THE INVENTION

In a preferred embodiment of the invention the antiglucocorticoid steroids according to the invention are 11β- or 10β-sustituted steroids having the general formula:

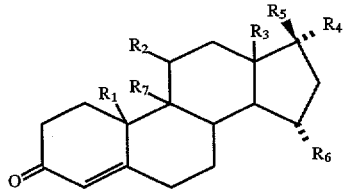

wherein:

$R_1$ is H, $CH_3$, unsubstituted or OH or halogen substituted $CH_2$=CH—$CH_2$ or CH≡C—$CH_2$, or an aryl, arylthio or arylmethyl group, the aryl moieties of which may optionally be substituted with (C1–C6) alkyl, (C1–C6) alkoxy, OH, halogen or $CF_3$, or $R_1$ together with $R_7$ is a bond;

$R_2$ is H, (C1–C6) alkyl or an aryl group optionally substituted with a group selected from (C1–C6) acyl, (C1–C6) alkoxy, (C1–C6) thioalkoxy, —O—$(CH_2)_n$—O—, n being 1 or 2, and

X and Y each being independently H or a group selected from (C1–C6) alkyl and (C1–C6) acyl, or $R_2$ together with $R_7$ is a bond;

$R_3$ is (C1–C6) alkyl;

$R_4$ is H, OH, (C1–C6) alkoxy, (C1–C6) acyloxy, a group selected from (C1–C6) alkyl, (C1–C6) alkenyl and (C1–C6) alkynyl, each of which group may be substituted with hydroxy, oxo, halogen, azido or cyano, or —C≡C-phenyl, the phenyl group of which may optionally be substituted with —S(O)m—(C1–C6) alkyl, m being 1 or 2, or with

X and Y each being independently H or a group selected from (C1–C6) alkyl and (C1–C6) acyl, or X and Y together with the nitrogen to which they are bonded form a ring;

$R_5$ is OH or a group selected from (C1–C6) acyloxy, (C1–C6) alkoxy or (C1–C6) acyl, each of which group may optionally be substituted with hydroxy, (C1–C6) alkoxy, (C1–C6) acyloxy or halogen; or $R_4$ and $R_5$ together with the carbon atom to which they are bonded form a 5- or 6-membered ring system;

$R_6$ is H or methyl optionally substituted with hydroxy or (C1–C6) alkoxy;

$R_7$ forms a bond with either $R_1$ or $R_2$.

In a more preferred embodiment the steroids have abovementioned formula wherein $R_1$ together with $R_7$ is a bond, $R_2$ represents a phenyl group which is substituted in the para position with an amino group

$R_3$ is methyl or ethyl, $R_4$ is prop-1-ynyl, $R_5$ is hydroxy and $R_6$ is H, hydroxymethyl or methoxymethyl.

In particular 11βB-(4-dimethylaminophenyl)-17β-hydroxy-17α-(prop-1-ynyl)-estra-4,9-dien-3-one (RU38486) is a preferred steroid.

Other preferred steroids are (11β,17α)-11,21-bis[4-(dimethylamino)phenyl]-17-hydroxy-19-norpregna-4,9-dien-20-yn-3-one, (11β,17α)-11-[4-(dimethylamino)phenyl]-17-hydroxy-21-[4-(1-pyrrolidinyl)phenyl]-19-norpregna-4,9-dien-20-yn-3-one, (11β,17α)-11-(1,3-benzodioxol-5-yl)-21-[4-(dimethylamino)phenyl]-17-hydroxy-19-norpregna-4,9-dien-20-yn-3-one, and (11β,17α)-11-[4-(dimethylamino)phenyl]-17-hydroxy-21-[4-(methylsulfonyl)phenyl]-19-norpregna-4,9-dien-20-yn-3-one.

The aryl group in the definition of $R_1$ may be derived from benzene, naphthalene or a 5- or 6-membered heteroaryl which comprises 1 to 4 hetero atoms selected from N, O and S. Preferably the aryl group is phenyl.

In the definition of $R_2$ the aryl group may be derived from, for example, benzene, biphenyl, naphthalene, anthracene or phenantrene. Phenyl is the preferred group. In particular a phenyl group is preferred, which is substituted in the para position with the

group or in the meta position with $OCH_3$ or $SCH_3$.

The (C1–C6) alkyl group is a branched or unbranched alkyl group having 1–6 carbon atoms, such as methyl, ethyl, propyl, butyl, isopropyl, pentyl, isopentyl, hexyl, tert-butyl and the like. Preferred alkyl groups have 1–4 carbon atoms; most preferred is the methyl group.

The (C2–C6) alkenyl group is a branched or unbranched alkenyl group having 2–6 carbon atoms, such as vinyl, 2-propenyl, 1,3-butadienyl and the like.

The (C2–C6) alkynyl group is a branched or unbranched alkynyl group having 2–6 carbon atoms, such as ethynyl, propynyl, butynyl, and the like. Most preferred is the prop-1-ynyl group.

The (C1–C6) alkylidene group is a branched or unbranched alkylidene group having 1–6 carbon atoms, such as ethylidene, propylidene, 2-methylpropylidene and the like.

The (C1–C6) alkoxy group is an alkoxy group of which the alkyl moiety is the (C1–C6) alkyl group as previously defined.

The (C1–C6) thioalkoxy group is an —S-alkyl group of which the alkyl moiety is the (C1–C6) alkyl group as previously defined.

The arylthio and arylmethyl groups, are arylthio and arylmethyl groups the aryl moiety of which is derived from benzene, naphthalene or a 5- or 6-membered heteroaryl which comprises 1 to 4 hetero atoms selected from N, O and S. Preferably the aryl moiety is phenyl.

The (C1–C6) acyl group is a branched or unbranched acyl group having 1–6 carbon atoms, such as formyl, acetyl, propionyl, butyryl and the like.

The (C1–C6) acyloxy group is a branched or unbranched acid ester group derived from a carboxylic acid having 1–6 carbon atoms, such as the ester group derived from formic acid, acetic acid, propionic acid and the like.

The term halogen means Cl, Br, F, or I. In particular F and Cl are preferred halogens.

When X and Y together with the nitrogen to which they are bonded form a ring, this ring is a saturated 5- or 6-membered ring, which may comprise a second heteroatom selected from N, O and S. Examples are pyrrolidinyl, piperidinyl, piperazinyl, and morpholinyl.

When $R_4$ and $R_5$ together represent a 5- or 6-membered ring system, this ring system can be a homo- or heterocyclic ring system with 5 or 6 atoms in the ring, the carbon atom at position 17 of the steroid skeleton being one of these 5 or 6 atoms. Preferably the ring system comprises at least one oxygen atom in the ring which oxygen atom is bonded to the carbon atom at position 17 of the steroid skeleton. In particular 5-membered heterocyclic ring systems having the following structures are preferred:

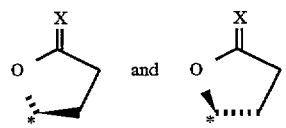

wherein the carbon atom which is provided with an * being the carbon atom in position 17 of the steroid skeleton, and X is $H_2$, [H,(C1–C6) acyloxy], [H,(C1–C6) hydrocarbyl] or oxygen. (C1–C6) hydrocarbyl means a hydrocarbon group having 1–6 carbon atoms such as (C1–C6) alkyl, (C1–C6) alkenyl, or (C1–C6) alkynyl, as previously defined.

The antiglucocorticoid steroids according to the invention can be prepared by suitable techniques known in the art, for example as described in BE-A-862869, DE-OS-3307143, EP-A-188396, EP-A-57115 and J. of Steroid Bioch. 31:567–571 (1988), which are incorporated by reference.

The antiglucocorticoid steroids according to the invention can be administered enterally or parentally, and for humans preferably in a daily dosage of 0.001–10 mg per kg body weight. Mixed with pharmaceutically suitable auxiliaries, e.g. as described in the standard reference, Genarro et al., Remington's Pharmaceutical Sciences, (18th ed., Mack Publishing Company, 1990, see especially Part 8: Pharmaceutical preparations and their manufacture), the steroids may be compressed into solid dosage units, such as pills, tablets, or be processed into capsules or suppositories. By means of pharmaceutically suitable liquids the steroids can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples without being limited thereto.

EXAMPLE 1

Antagonism of Stress Induced Hyperthermia

Rectal temperature measurement induces a stress reaction, which results in a rise in body temperature. This rise in temperature can be inhibited by anxiolytic drugs. The rise in temperature after treatment with a drug, expressed as percentage of the rise in temperature after treatment with a placebo, is an indication for the anxiolytic effect of the compound. Animals are pretreated with reserpine to lower their body temperature and make the stress induced temperature rise more apparent.

1.1 Animals

Male mice (Crl: CD-1 (ICR) BR, from Charles River, Germany) weighing 20–30 g were used. They were kept in a temperature controlled room (21°–23° C.) under a fixed 12 h light-dark cycle. Food pellets and drinking solution were available ad libitum.

1.2 Measurement of rectal temperature

The body temperature was measured per rectum using an electrothermometer (Ellab TE3, Electrolaboratoriet, Copenhagen, Denmark), lubricated with Vaseline grease. The probe was inserted to a depth of approximately 2.5 cm and left until the temperature indication was constant.

1.3 Drugs

The drugs used were RU38486; 11β-(4-dimethylaminophenyl)-15α-hydroxymethyl-17α-(prop-1-ynyl)-17β-hydroxy-estra-4,9-dien-3-one (A); 11β-(4-dimethylaminophenyl)-15α-methoxymethyl-17α-(prop-1-ynyl)-17β-hydroxy-estra-4,9-dien-3-one (B); (11β,17α)-11,21-bis[4-(dimethylamino)phenyl]-17-hydroxy-19-norpregna-4,9-dien-20-yn-3one (C); (11β,17α)-11-[4-(dimethylamino)phenyl]-17-hydroxy-21-[4-(1-pyrrolidinyl)phenyl]-19-norpregna-4,9-dien-20-yn-3-one (D); (11β,17α)-11-(1,3-benzodioxol-5-yl)-21-[4-(dimethylamino)phenyl]-17-hydroxy-19-norpregna-4,9-dien-20-yn-3-one (E); and (11β,17α)-11-[4-(dimethylamino)phenyl]-17-hydroxy-21-[4-(methylsulfonyl)phenyl]-19-norpregna-4,9-dien-20-yn-3-one (F). Drugs were used in dosages between 0.32 mg/kg and 32 mg/kg. For comparison librium and valium were used in dosages of 1 mg/kg, 3.2 mg/kg and 10 mg/kg. The drugs were dissolved in mulgophen/NaCl and administered at a volume of 10 ml/kg.

1.4 Procedure

The mice were pretreated with 2 mg/kg (s.c.) of reserpine (monoamine depletor). The reserpine induced a decrease in body temperature. After 17 hours the body temperature was measured rectally, which gave the baseline value. Thirty minutes after baseline measurement the drugs were administered subcutaneously and at t=30, 60, 120, 180, and 240 min the temperature was measured. The rise in temperature at t=120 min and at t=240 min due to the stress reaction was expressed as percentage of the temperature rise of the placebo at t=120 min and t=240 min respectively. These percentages are presented in Table 1.

TABLE 1

Temperature rise in mice after treatment with antiglucocorticoid steriods, expressed as percentage of the rise in temperature observed after treatment with a placebo. The rise in temperature is measured at t = 120 (between brackets the temperature rise at t = 240 min) at various dosages of drugs administered.

| | dosage in mg/kg | | | | |
|---|---|---|---|---|---|
| | 0.32 | 1 | 3.2 | 10 | 32 |
| RU38486 | — | — | 70(98) | 83(89) | 71(74) |
| steroid A | — | — | 42(58) | 48(54) | 66(71) |
| steroid B | — | — | 63(32) | 67(38) | 49(37) |
| steroid C | 33(50) | 57(94) | 11(9) | — | — |
| steroid D | 102(102) | 61(85) | 84(109) | — | — |
| steroid E | 73(97) | 59(91) | 57(104) | — | — |
| steroid F | 84(87) | 58(43) | 115(127) | — | — |
| librium | — | 67(69) | 48(87) | 33(30) | — |
| valium | — | 20(3) | 7(2) | 37(11) | — |

As can be seen from the results of Table 1, the antiglucocorticoid steroids considerably reduce the rise in temperature. The observed effect on the stress reaction is comparable to the effect resulting from treatment with librium and valium respectively.

EXAMPLE 2

Anxiety Test

The (Borsini) anxiety test (Psychopharmacology 98:207–211, 1989) is based on the fact that among animals from the same cage, those removed last have a higher body temperature as compared to those removed first. This phenomenon can also be observed by reversing the order of removal of the animals from the cage and can therefore be interpreted as an indication of a state of anxiety due to expectation of a (known or unknown) event. The observed rise in body temperature can be prevented by the administration of anxiolytic drugs. This test is useful in demonstrating the anxiolytic effect of compounds.

2.1 Animals

Male mice (Crl: CD-1 (ICR) BR, from Charles River, Germany) weighing 20–30 g were used. They were kept in a temperature controlled room (21°–23° C.) under a fixed 12 h light-dark cycle. All animals were housed in macrolon cages; 10 animals per cage. Food pellets and water were available ad libitum. Prior to the experiments the animals were allowed to adapt to the environment for at least 14 days.

2.2 Temperature measurement

The body temperature was measured per rectum using an electrothermometer (Ellab TE3, Electrolaboriet, Copenhagen, DK), lubricated with Vaseline grease. The probe was inserted to a depth of approximately 2.5 cm and left until the temperature indication was constant.

2.3 Drugs

The used drug was RU38486 in dosages of 3.2, 10, and 32 mg/kg. RU38486 was dissolved in mulgophen/NaCl and injected at t=−30 min. The drug was administered at a volume of 10 ml/kg.

2.4 Procedure

The methodology was similar to that described by Borsini et al (Psychopharmacology 98:207–211, 1989). In short, at t=0 min all mice were injected subcutaneously. At t=30 min the temperature of the first and the last three mice was measured. Mouse 4 to 7 were simply removed. Furthermore the behavioural activity of mouse 10 was determined by behavioural observations. Effects were evaluated by subtracting the mean body temperature of the first three mice from the mean temperature of the last three mice. Comparison between placebo and treatment group were made by means of Mann Whitney-U tests.

2.5 Results

RU38486 in a dosage of 3.2 mg/kg reduced the temperature difference between the first and the last three mice significantly. The results are presented in FIG. 1.

EXAMPLE 3

Antagonism of the Fear Potentiated Startle

The fear potentiated startle is a well known paradigm to evaluate anxiolytic drugs (Davis, Behavioral Neuroscience 100 (1986) 814–824). In this paradigm rats are trained to associate a light with the presentation of footshocks. Acoustic noise bursts normally elicit a startle reaction; this reaction is increased when the noise burst is presented in the presence of the light. The fear potentiated startle phenomenon can be inhibited by anxiolytics in the non-sedative dose-range.

3.1 Animals

Male rats (Wistars, HSD/Cpb: Wu, Harlan Sprague Dawley, Zeist, The Netherlands) weighing 275–300 g were used.

They were housed in groups of 5 (in 40 * 40 * 17 cm cages) at a room temperature of 21°–23° C. They were exposed to a normal 12-h light-dark cycle (lights on at 6.00 h) and had free access to food and water.

3.2 Measurement of startle reflexes

The apparatus used was an SRLAB system (San Diego Instruments, San Diego, Calif., USA). The system consisted of eight startle boxes, which contained each a cylindrical tube resting on a piezoelectric accelerometer for detecting total body-activity within the Plexiglas tube. Reflex amplitude was measured during the 200 ms interval following the presentation of the stimulus. The acoustic noise bursts (120 dB) and background noise (70 dB) were presented by a loudspeaker, mounted 24 cm above the animal. For the fear potentiated startle session a stainless steel shock grid, which was power-supplied by a Coulbourn Animal shocker, was placed into each Plexiglas tube.

The startle boxes were sound-tight and isolated from each other. Between test sessions, the cages were cleaned thoroughly using water and non-perfumed soap.

3.3 Drugs

The drug used was RU38486 in a dosages of 3.2 mg/kg. RU38486 was dissolved in mulgophen/NaCl and administered at a volume of 5 ml/kg.

3.4 Procedure

For two days, rats were placed in the startle boxes in which the shock grids were installed. They were conditioned using a session of 15 trials, in which a signal of 3 seconds light was linked to a 1 mA shock during 0.5 s.

On day 3 the animals were injected with the compound or placebo and were placed in the startle boxes 90 min later. They were, after an acclimatisation period of 5 min (background noise only) confronted with 60 acoustic noise bursts (25 ms duration). Bursts were separated by an interval of 15 s. Data were averaged over blocks of 5 trials.

3.5 Results

RU38486 (3.2 mg/kg) reduced the amplitude of the fear potentiated startle. The results are presented in FIG. 2.

EXAMPLE 4

A pharmaceutical composition based on RU38486 for the treatment of anxiety disorders was prepared and comprises 50 mg of RU38486 and additives (talc, polyvinylpyrrolidone and magnesium stearate) up to a total weight of 120 mg.

EXAMPLE 5

(11β,17α)-11,21-Bis[4-(dimethylamino)phenyl]-17-hydroxy-19-norpregna-4,9,dien-20-yn-3-one a) 27 g (100 mmol) of estra-4,9-diene-3,17-dione, dissolved in 270 ml of tetrahydrofuran (THF) and 270 ml of methanol, were cooled to −10° C. and treated with 2.27 g (60 mmol) of sodium borohydride. The solution was stirred for 30 min at −10° C. Work-up was accomplished by dropwise addition of 8 ml of 50% acetic acid. The mixture was extracted with ethyl acetate, the organic layers were washed with brine, dried on anhydrous magnesium sulfate, filtered and evaporated to dryness resulting in 27.2 g of 17β-hydroxy-estr-4,9-diene-3-one.

b) 25 g of the obtained material were dissolved in 375 ml of dichloromethane; 125 ml of ethylene glycol, 75 ml of trimethylorthoformate and 250 mg of p-toluenesulfonic acid were added and the mixture was refluxed for 20 min. After cooling, 200 ml of a saturated sodium hydrogen carbonate solution were added and the resulting mixture was extracted with dichloromethane. Evaporation in vacuo followed by purification of the resulting oil by column chromatography using silicagel, provided 19.9 g of 17α-hydroxy-estra-5(10),9(11)-diene-3-one 3-(cyclic 1,2-ethanediyl acetal) as an oil.

c) 19.9 g (62.9 mmol) of 17α-hydroxy-estra-5(10),9(11)-diene-3-one 3-(cyclic 1,2-ethanediyl acetal) were dissolved in 400 ml of dichloromethane. 27.6 g (336 mmol) of sodium acetate were added followed by 36.2 (168 mmol) of pyridinium chlorochromate and the mixture was stirred at ambient temperature. After 2 hours, 43.5 ml of 2-propanol were added and stirring was continued for 1 hour. The mixture was filtered over celite, evaporated and partitioned between ethyl acetate (1350 ml) and water (675 ml). The organic layer was separated, washed with brine, dried with anhydrous magnesium sulfate and filtered. Evaporation followed by purification by column chromatography using silicagel provided 10.9 g of estra-5(10),9(11)-diene-3,17-dione 3-(cyclic 1,2-ethanediyl acetal). Melting point: 152° C.

d) A mixture of 13 g (116.2 mmol) of potassium tert. butoxide, 55 ml of THF and 18.7 ml of tert. butanol was cooled to 0°–5° C. under inert atmosphere. Acetylene was bubbled through the mixture for one hour; then 9.43 g (30 mmol) of estra-5(10),9(11)-diene-3,17-dione 3-(cyclic 1,2-ethanediyl acetal), dissolved in 50 ml of THF were added. Stirring was continued for 1.5 hrs at 0°–5° C. under acetylene atmosphere. Work-up was accomplished by pouring the mixture into a saturated aqueous ammonium chloride solution, followed by ethyl acetate extraction. The organic layers were washed with brine, dried with anhydrous magnesium sulfate, filtered and evaporated to give 10.4 g of 17α-ethynyl-17β-hydroxy-estra-5(10),9(11)-diene-3-one 3-(cyclic 1,2-ethanediyl acetal).

e) 10 g (29.4 mmol) of 17α-ethynyl-17β-hydroxy-estra-5(10),9(11)-diene-3-one 3-(cyclic 1,2-ethanediyl acetal) were dissolved in 150 ml of dichloromethane. Subsequently 0.91 ml of pyridine, 2.84 ml of trifluoroacetophenone and 18.8 ml of 30% hydrogen peroxide were added and the resulting two-phase system was vigorously stirred at room-temperature for 36 hrs. The mixture was poured into water and the organic layer was washed twice with a saturated sodium thiosulfate solution. Drying with anhydrous magnesium sulfate, filtering and evaporation provided a semi-solid mass consisting of a mixture of epoxides. Trituration with toluene afforded 4.22 g of 5α,10α-epoxy-17α-ethynyl-17β-hydroxy-estr-9(11)-ene-3-one 3-(cyclic 1,2-ethanediyl acetal).

f) 158 mg of CuCl were added at 0°–5° C. to a solution of p-dimethylaminophenylmagnesium bromide in THF, prepared from 1.49 g of magnesium (61 mmol), 30 ml of THF and 11.8 g (58.9 mmol) of 4-bromo-N,N-dimethylaniline. After stirring for 30 min at 0°–5° C., 4.2 g of 5α,10α-epoxy-17α-ethynyl-17β-hydroxy-estr-9(11)-ene-3-one 3-(cyclic 1,2-ethanediyl acetal) in 42 ml of THF were added dropwise. After being stirred for 2.5 hrs at ambient temperature, the solution was poured into a saturated ammonium chloride solution and extracted with ethyl acetate. The organic layers were washed until neutral, dried with anhydrous magnesium sulfate, filtered and evaporated in vacuo and the residue was chromatographed using silicagel. This provided after crystallization from ether/heptane 3.2 g of pure 5α,17β-dihydroxy-11β-[4-(N,N-dimethylamino)phenyl]-17α-ethynyl-estr-9-ene-3-one 3-(cyclic 1,2-ethanediyl acetal). Melting point: 198° C.

g) 3.0 g (6.3 mmol) of 5α,17β-dihydroxy-11β-[4-(N,N-dimethylamino)phenyl]-17α-ethynyl-estr-9-ene-3-one 3(cyclic 1,2-ethanediyl acetal) were dissolved in 39 ml of pyrrolidine. Subsequently 1.26 g of 4-bromo-N,N-dimethylaniline (6.3 mmol), 33 mg of palladium(II) acetate, 33 mg of copper(I) iodide and 99 mg of triphenylphosphine were added and the mixture was refluxed for one hour under inert atmosphere. After cooling, the mixture was poured into a 50% aqueous ammonium chloride solution and extracted with ethyl acetate. The organic layers were washed with brine, dried with anhydrous magnesium sulfate, filtered and evaporated to dryness, yielding a crystalline mass. Trituration with diethyl ether provided 2.45 g of pure 11,21-bis[(dimethylamino)phenyl-]5α,17β-dihydroxy-pregn-9-ene-20-yn-3-one (cyclic 1,2-ethanediyl acetal). Melting point: 150° C.

h) 2.45 g (4.0 mmol) of 11,21-bis[(dimethylamino) phenyl]-5α,17β-dihydroxy-pregn-9-ene-20-yn-3-one (cyclic 1,2-ethanediyl acetal) were dissolved in 123 ml of acetone and with stirring 4.9 ml 6N HCl were added. After stirring for 30 min at ambient temperature, the mixture was neutralized with sodium hydrogen carbonate, followed by extraction with ethyl acetate. The organic layer was washed until neutral, dried with anhydrous magnesium sulfate, filtered and evaporated in vacuo. The residue was purified by column chromatography using silicagel. This afforded 1.2 g of pure (11β,17α)-11,21-bis[4-(dimethylamino)phenyl]-17-hydroxy-19-norpregna-4,9-dien-20-yn-3-one. $[\alpha]^{20}_D = -12°$ (c=1, chloroform).

EXAMPLE 6

The following products were prepared from 5α,17β-dihydroxy-11β-[4-(N,N-dimethylamino)phenyl]-17α-ethynyl-estr-9-ene-3-one 3-(cyclic 1,2-ethanediyl acetal) (see example 5f) by using the appropriate starting material for the Heck coupling reaction (according to the procedure of example 5g), followed by the acidic dehydration and deprotection as described in example 5h:

A using 4-bromo-(1-pyrrolidinyl)benzene the reaction resulted in (11β,17α)-11-[4-(dimethylamino)phenyl]-17-hydroxy-21-[4-(1-pyrrolidinyl)phenyl]-19-norpregna-4,9-dien-20-yn-3-one having a specific rotation of $[\alpha]^{20}_D = -19°$ (c=1, chloroform).

B using 4-bromo-(methylsulfonyl)benzene the reaction resulted in (11β,17α)-11-[4-(dimethylamino)phenyl]-17-hydroxy-21-[4-(methylsulfonyl)phenyl]-19-norpregna-4,9-dien-20-yn-3-one having a specific rotation of $[\alpha]^{20}_D = -23°$ (c=0.5, dioxane).

EXAMPLE 7

According to the procedure described in example 5f, the Cu-catalyzed Grignard reaction of 3,4-methylenedioxophenylmagnesium bromide with 5α,10α-epoxy-17α-ethynyl-17β-hydroxy-estr-9(11)-ene-3-one 3-(cyclic 1,2-ethanediyl acetal) provided 5α,17β-dihydroxy-17α-ethynyl-11β-(1,3-benzodioxol-5-yl)-estr-9-ene-3-one 3-(cyclic 1,2-ethanediyl acetal). Melting point: 155° C.

By using 4-bromo-N,N,-dimethylaniline for the Heck coupling reaction (according to the procedure of example 5g), followed by the acidic dehydration and deprotection as described in example 5h was prepared (11β,17α)-11-(1,3-benzodioxol-5-yl)-21-[4-(dimethylamino)phenyl]-17-hydroxy-19-norpregna-4,9-dien-20-yn-3-one; $[\alpha]^{20}_D = -63°$ (c=1, chloroform).

I claim:

1. A method for the treatment of anxiety disorders, comprising administering an anxiolytically effective amount of at least one antiglucocorticoid steroid.

2. The method according to claim 1, wherein the antiglucocoticoid steroid has the general formula

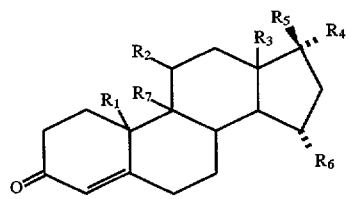

wherein

R₁ is H, CH₃, unsubstituted or OH or halogen substituted CH₂=CH—CH₂ or CH=C—CH₂, or an aryl, arylthio or arylmethyl group, the aryl moieties of which may optionally be substituted with (C1–C6) alkyl, (C1–C6) alkoxy, OH, halogen or CF₃, or R₁ together with R₇ is a bond;

R₂ is H, (C1–C6) alkyl or an aryl group optionally substituted with a group selected from (C1–C6) acyl, (C1–C6) alkoxy, (C1–C6) thioalkoxy, —O—(CH₂)ₙ—O—, n being 1 or 2, and

X and Y each being independently H or a group selected from (C1–C6) alkyl and (C1–C6) acyl, or R₂ together with R₇ is a bond;

R₃ is (C1–C6) alkyl;

R₄ is H, OH, (C1–C6) alkoxy, (C1–C6) acyloxy, a group selected from (C1–C6) alkyl, (C1–C6) alkenyl and (C1–C6) alkynyl, each of which group may be substituted with hydroxy, oxo, halogen, azido or cyano, or —C≡C-phenyl, the phenyl group of which may optionally be substituted with S—(O)m—(C1–C6) alkyl, m being 1 or 2, or with

X and Y each being independently H or a group selected from (C1–C6) alkyl and (C1–C6) acyl, or X and Y together with the nitrogen to which they are bonded form a ring;

R₅ is OH or a group selected from (C1–C6) acyloxy, (C1–C6) alkoxy or (C1–C6) acyl, each of which group may optionally be substituted with hydroxy, (C1–C6) alkoxy, (C1–C6) acyloxy or halogen; or R₄ and R₅ together with the carbon atom to which they are bonded form a 5- or 6-membered ring system;

R₆ is H or methyl optionally substituted with hydroxy or (C1–C6) alkoxy; and

R₇ forms a bond with either R₁ or R₂.

3. The method according to claim 2, wherein said steroid is selected from 11β-(4-dimethylaminophenyl)-17β-hydroxy-17α-(prop-1-ynyl)-estra-4,9-dien-3-one (RU38486), (11β,17α)-11,21-bis[4-(dimethylamino) phenyl]-17-hydroxy-19-norpregna-4,9-dien-20-yn-3-one, (11β,17α)-11-[4-(dimethylamino)phenyl]-17- hydroxy-21-[4-(1-pyrrolidinyl)phenyl]-19-norpregna-4,9-dien-20-yn-3-one, (11β,17α)-11-(1,3-benzodioxol-5-yl)-21-[4-(dimethylamino)phenyl]-17-hydroxy-19-norpregna-4,9-dien-20-yn-3-one, and (11β,17α)-11-[4-(dimethylamino)phenyl]-17-hydroxy-21-[4-(methylsulfonyl)phenyl]-19-norpregna-4,9-dien-20-yn-3-one.

* * * * *